(12) United States Patent
Choi et al.

(10) Patent No.: US 8,962,567 B2
(45) Date of Patent: Feb. 24, 2015

(54) EYE DROP COMPOSITION FOR PREVENTION AND TREATMENT OF OPHTHALMIC DISEASES CONTAINING FUSION PROTEIN OF FK506 BINDING PROTEIN

(75) Inventors: Soo Young Choi, Gangwon-do (KR); Dae Won Kim, Chuncheon-si (KR); Sung Ho Lee, Seoul (KR); Jinseu Park, Gangwon-do (KR); Won Sik Eum, Gangwon-do (KR)

(73) Assignee: Industry Academic Cooperation Foundation, Hallym University, Gangwon-do (KR)

( * ) Notice: Subject to any disclaimer, the term of this patent is extended or adjusted under 35 U.S.C. 154(b) by 17 days.

(21) Appl. No.: 13/985,845

(22) PCT Filed: Apr. 6, 2011

(86) PCT No.: PCT/KR2011/002393
§ 371 (c)(1),
(2), (4) Date: Aug. 15, 2013

(87) PCT Pub. No.: WO2012/111877
PCT Pub. Date: Aug. 23, 2012

(65) Prior Publication Data
US 2013/0330368 A1 Dec. 12, 2013

(30) Foreign Application Priority Data
Feb. 15, 2011 (KR) .................. 10-2011-0013166

(51) Int. Cl.
| | |
|---|---|
| *A61K 38/00* | (2006.01) |
| *A61P 27/02* | (2006.01) |
| *C12N 9/90* | (2006.01) |
| *A61K 38/16* | (2006.01) |
| *A61K 38/52* | (2006.01) |
| *C07K 7/06* | (2006.01) |
| *C07K 14/00* | (2006.01) |

(52) U.S. Cl.
CPC . *C12N 9/90* (2013.01); *A61K 38/16* (2013.01); *A61K 38/00* (2013.01); *A61K 38/52* (2013.01); *C12Y 502/01008* (2013.01); *C07K 7/06* (2013.01); *C07K 14/001* (2013.01); *C07K 2319/00* (2013.01); *C07K 2319/10* (2013.01); *Y10S 514/914* (2013.01)
USPC ........................................ 514/20.8; 514/914

(58) Field of Classification Search
None
See application file for complete search history.

(56) References Cited

U.S. PATENT DOCUMENTS

| | | | |
|---|---|---|---|
| 7,902,346 B2 * | 3/2011 | Choi et al. .................. | 536/23.1 |
| 2003/0228299 A1 | 12/2003 | Droy-Lefaix et al. | |
| 2006/0258698 A1 | 11/2006 | Mudumba et al. | |

FOREIGN PATENT DOCUMENTS

| | | | |
|---|---|---|---|
| KR | 10-2004-0075236 A | 8/2004 | |
| KR | 10-0472938 B1 | 2/2005 | |
| KR | 10-0490362 B1 | 5/2005 | |
| KR | 10-0787393 B1 | 12/2007 | |
| WO | PCT/KR2007/001144 | * 9/2007 | ............. C07K 19/00 |

OTHER PUBLICATIONS

Walker, et al., "Enzyme-linked immunosorbent assay (ELISA)" Methods in Molecular Biology, vol. 1, Humana Press, NJ 1984, pp. 349-353.
Johnson, et al., "Effectiveness of sodium hyaluronate eyedrops in the treatment of dry eye," Graefe's Arch Clin Exp Ophthalmol (2006) 244: 109-112.
Johnson, et al., "Carbomer and Sodium Hyaluronate Eyedrops for Moderate Dry Eye Treatment," Optometry and Vision Science, vol. 85, No. 8, Aug. 2008, pp. 750-757.
Fujihara, et al., "Improvement of Corneal Barrier Function by the P2Y2 Agonist INS365 in a Rat Dry Eye Model," Investigative Ophthalmology & Visual Science, Jan. 2001, vol. 42, No. 1, 96-100.
Nakamura, et al., "Development of a Rabbit Model of Tear Film Instability and Evaluation of Viscosity of Artificial Tear Preparations," Cornea • vol. 23, No. 4, May 2004, pp. 390-397.
Nakamura, et al., "The Sucessful Culture and Autologous Transplantation of Rabbit Oral Mucosal Epithelial Cells on Amniotic Membrane," Investigative Ophthalmology & Visual Science, Jan. 2003, vol. 44, No. 1, pp. 106-116.
Higuchi, et al., "Albumin Rescues Ocular Epithelial Cells from Cell Death in Dry Eye," Current Eye Research, 2007, 32, pp. 83-88.
Barrett, et al., "Advances in Cytochemical Methods for Detection of Apoptosis", The Journal of Histochemistry & Cytochemistry vol. 49(7): 821-832, 2001.
Yeb, et al., "Apoptosis of Ocular Surface Cells in Experimentally Induced Dry Eye," Investigative Ophthalmology & Visual Science, Jan. 2003, vol. 44, No. 1, 124-129.
Yokoi, et al., "Clinical Evaluation of Corneal Epithelial Barrier Function with the Slit-Lamp Fluorophotometer," Cornea 14(5); 485-489, 1995.
Nakamura, et al., "Characterization and Distribution of Bone Marrow-Derived Cells in Mouse Cornea," Investigative Ophthalmology & Visual Science, Feb. 2005, vol. 46, No. 2, 497-503.

(Continued)

*Primary Examiner* — Karlheinz R Skowronek
*Assistant Examiner* — Joseph Fischer
(74) *Attorney, Agent, or Firm* — Knobbe, Martens, Olson & Bear, LLP

(57) ABSTRACT

Disclosed is a treatment for ophthalmic diseases, more specifically, a pharmaceutical composition for treating ophthalmic diseases including a fusion protein of FK506 binding protein capable of penetrating into the ocular tissue as an active ingredient.

10 Claims, 2 Drawing Sheets

(56) References Cited

OTHER PUBLICATIONS

Steinfeld, et al., "Bioavailability of flourescein from a new drug delivery system in human eyes," Br J Ophthalmol 2004;88:48-53.
Koh, et al., "Diagnosing Dry Eye Using a Blue-free Barrier Filter," American Journal of Ophthalmology Sep. 2003, vol. 136, No. 3, pp. 513-519.
Kang, et al., "FKBP Family Proteins: Immunophilins with Versatile Biological Functions," Neurosignals 2008,16, pp. 318-325.
Chelu, et al., "Regulation of Ryanodine Receptors by FK506 Binding Proteins," TCM vol. 14, No. 6, 2004, pp. 227-234.
International Search Report dated Feb. 24, 2012 for International Patent Application No. PCT/KR2011/002393.

* cited by examiner

EYE DROP COMPOSITION FOR PREVENTION AND TREATMENT OF OPHTHALMIC DISEASES CONTAINING FUSION PROTEIN OF FK506 BINDING PROTEIN

TECHNICAL FIELD

The present disclosure relates to a treatment for ophthalmic diseases, and more particularly, to a pharmaceutical composition for treatment of ophthalmic diseases containing a transducible fusion protein of FK506 binding protein (FK506BP) as an active ingredient.

BACKGROUND ART

Recently, the use of immunosuppressants in ophthalmic clinics is increasing because of increased corneal transplantation and autoimmune disease, and new drugs are actively being developed to reduce adverse effects of the immunosuppressants. Immunosuppressants for ophthalmic diseases are generally formulated as eye drop preparations. Since currently used drugs do not penetrate the cornea well, they must be used in large quantities, which results in adverse effects. The cornea is permeable to amphiphilic drugs containing hydrophilic and lipophilic moieties.

Corneal transplantation is a surgical procedure in which a damaged or diseased cornea of a patient is replaced with a donor cornea to restore vision. With advances in corneal preservation methods, surgical techniques and surgical devices as well as inhibition of corneal transplant rejection, corneal transplantation has become the most frequently performed transplantation surgery globally. Since corneas remain transplant viable even after cardiopulmonary function has stopped, it is more successful than other organs and is the only actively performed organ transplantation in Korea where brain death is not legally accepted. According to the Korean Network for Organ Sharing, the number of corneal transplants performed each year is on the rise, with 405 corneal transplants being performed in 2007. In the US, well over 40,000 corneal transplants have been performed in the period between 1990 and 2007.

As corneal transplantation has become increasingly common, several problems have arisen and efforts are underway to negate such problems. Corneal transplant rejection is an immune-mediated inflammatory response and accounts for the majority of corneal transplant failure. Steroids have been used to reduce corneal transplant rejection. However, long-term use of steroids may result in increased intraocular pressure, delayed wound healing, complications such as cataracts and even high doses cannot stop rejection in certain high-risk individuals. Recently, efforts are underway to reduce rejection using immunosuppressants rather than steroids. It has been reported that, in groups at high-risk of corneal transplant rejection, those treated with the immunosuppressant cyclosporin A showed less rejection than those treated with steroids alone. In an animal model, a group treated with FK506 (tacrolimus) after corneal xenotransplantation was reported to show less inflammatory cell infiltration as compared to the untreated group. Although the use of FK506 or cyclosporin A in patients who have received organ transplants provides excellent immunosuppressive effects, adverse effects of the drugs such as the risk of nephrotoxicity, hypertension, metabolic disorders, diabetes, etc. are problems.

Autoimmune diseases occur when the body launches an immune system attack against its own tissues. Although it is thought that autoimmune diseases are associated with overactive or improper control of immune response induced by the change in the environment of cytokines (signaling molecules that control and stimulate the body's defense system) in the body against viruses or bacteria, its exact cause is not known. It is believed that environmental, genetic and immunological factors are involved. At present, more than 80 autoimmune diseases are known. According to a study in the US, the number of rheumatoid arthritis patients is 2.1 million, the number of fibromyalgia patients is 3.7 million, the number of psoriasis patients is 4-4.5 million, 10-30% of those also suffering from arthritic, the number of leukoplakia patients is 4 million, and the number of Sjogren syndrome patients is 2-3 million. Well-known autoimmune ophthalmic diseases include uveitis, Behcet's disease and keratoconjunctivitis. Recently, as xerophthalmia is identified as an immune-mediated inflammatory disease, it is also regarded as an autoimmune disease. Uveitis is a representative autoimmune ophthalmic disease. The uvea, which consists of the iris, the ciliary body and the choroid, is subject to inflammation because it is rich in blood vessels and connective tissues. Uveitis refers to inflammation of the uvea. At present, the cause of this disease is not certain, syphilis and tuberculosis being known as risk factors. Immune system abnormalities are suspected to be the cause of uveitis. Although inflammation of the uvea can also be caused by bacteria or viruses, it is classified as an autoimmune disease since there are many immunological inflammatory responses. Topical or systemic steroids have been used for treatment of uveitis. However, treatment with topical (e.g. eye drop) or systemic steroids requires high doses if the drug does not sufficiently reach the uveal tissue. In this case, severe adverse effect may occur. In patients who do not respond to steroid therapy or those who cannot endure the adverse effects of systemic steroids, immunosuppressants are used. However, even in this case, the treatment is often interrupted due to adverse effects such as bone marrow suppression, hemorrhagic cystitis, nephropathy, etc. As a result, patients frequently go blind. Accordingly, development of an eye drop for treatment of ophthalmic diseases transducing well into the eyes and having fewer adverse effects is needed.

Xerophthalmia (eye dryness) is a medical condition in which the eye fails to produce enough tears or the tear film becomes unstable due to excessive evaporation, causing foreign body sensation or irritation. That is to say, xerophthalmia occurs when secretion of tears is reduced or is accompanied by diseases of the eyeball and accessory organs, such as disorder or inflammation of the eyelid, skin diseases (e.g., Stevens-Johnson syndrome or pemphigoid), or systemic diseases (e.g., vitamin A deficiency or Sjogren syndrome) (Ophthalmology, 7th ed., Dong-Ho Yoon, Sang-Wook Lee, Ouk Choi, Ilchokak, 2005). According to a recent survey conducted by Chung-Ang University Hospital, 75% of Korean adults suffer from eye dryness, one out of three of those cases involving serious inflammation of the cornea.

For treatment of xerophthalmia, focus has made on supplementing artificial tears in the form of eye drops, or transiently or permanently blocking the lacrimal canals to keep the tears above a certain level. Recently, as xerophthalmia is newly recognized as an inflammatory disease, anti-inflammatory therapy for xerophthalmia is being investigated, and improvement of symptoms is reported in patients with severe eye dryness.

As the inflammatory changes of the ocular surface in xerophthalmia, including increased T lymphocytes, increased level of various inflammatory mediators including cytokines, or the like, are proven, suppression of inflammation on the ocular surface has become a main concern of xerophthalmia treatment. Cyclosporin A 0.05% eye drops (Restasis™) are one of such drugs. However, cyclosporin A frequently has adverse effects in xerophthalmia patients. The most common adverse reaction is a burning sensation of the eyes, and it is reported that 1-5% of patients suffer conjunctival hyperemia, secretion, epiphora, pain in the eyes, foreign body sensation, itching, stinging, vision disorder (often blurred vision), etc. Accordingly, development of new anti-inflammatory and immunosuppressant drugs with fewer adverse effects is needed.

Although use of immunosuppressants for ophthalmic diseases is increasing gradually, use thereof is restricted due to severe adverse effects. An immunosuppressant refers to any substance used to suppress the ability of the body to produce antibodies (humoral immunity) or to reduce or interrupt cell-mediated immunity. It is mainly used for treatment of autoimmune diseases, selective immunosuppression, e.g., in hemolytic diseases of newborns, and prevention of rejection after organ transplantation. Use of immunosuppressants is restricted because of adverse effects such as anemia, leukopenia, thrombocytopenia, hair loss, and so forth. Secondary metabolites from bacteria and fungi were developed as immunosuppressive agents with less cytotoxicity. Cyclosporin A and FK506 are typical examples widely used for organ transplant patients, but they still have adverse effects.

For treatment of ophthalmic diseases, change of the preparation form from a systemic one to an eye drop is required to reduce adverse effects of existing drugs. Recently frequently used immunosuppressants including cyclosporin and FK506 are used for systemic purposes. However, since both drugs may damage the kidneys and nerves, development of eye drop preparations is being carried out in order to reduce adverse effects while enhancing medicinal effects. It was reported that administration of FK506 as an eye drop preparation provides an excellent effect of delaying rejection after corneal transplantation. Further, it was reported that administration of FK506 as an eye drop preparation to xerophthalmia patients achieved better results than common eye dryness drugs. According to a report by the Department of Ophthalmology, Catholic University of Korea, administration of cyclosporin-containing eye drops to xerophthalmia patients for 3 months resulted in increased secretion of tears. Especially, the effect was better in those who had xerophthalmia accompanied by systemic diseases. However, this result is restricted in that the period of clinical testing was too short. A research team from the University of Pennsylvania School of Medicine reported in the *Journal of the American Medical Association* that administration of cyclosporin-containing eye drops was very effective for treatment of eye dryness in patients with moderate-to-severe xerophthalmia, which occur in 15-34% of the elderly.

Although the eye drop preparation is much more effective than that for systemic administration and is capable of minimizing adverse effects, introduction of a new technique is required since it is very difficult for the drug to penetrate into the eyes. Especially, protein drugs are much more difficult to deliver into the eyes. The delivery of the drug through the cornea is disturbed by many factors, including differences in the chemical compositions of the epithelium and stroma of the cornea. Whereas the corneal epithelium is rich in lipids and is more permeable to undissociable drugs, the corneal stroma passes only dissociable ones. In addition, the corneal endothelium, which is rich in lipoids, passes only lipophilic substances. Thus, the cornea tends to be permeable to amphiphilic drugs which have both lipophilic and hydrophilic moieties. For this reason, an excessive amount has to be administered if the associated drug cannot penetrate the cornea well, which may cause adverse effects.

Korean Patent No. 472938 relates to a transport domain-target protein-transport domain fusion protein with advanced cell-transducing efficiency and uses thereof. There is disclosed an advanced cell-transducing fusion protein in which a protein transport domain such as HIV-1 Tat peptide, oligolysine or oligoarginine is covalently bonded to the N-terminal and/or C-terminal of a target protein.

Korean Patent No. 490362 discloses a complex wherein oligolysine is covalently bonded as a protein transducing domain to the N-terminal and/or C-terminal of a protein in order to improve cell transduction.

Through extensive research, including the above patents, it was found out that HIV-a Tat peptide, oligolysine, oligoarginine, oligo(lysine/arginine), PEP-1 peptide, and the like improve cellular transduction of proteins.

In addition, Korean Patent No. 787393 discloses an FK506 binding protein (FK506BP) fusion protein and a composition for improving atopic dermatitis and allergy comprising the same.

However, nothing is known about the use of FK506BP or FK506BP fusion protein for prevention or treatment of ophthalmic diseases.

DISCLOSURE

Technical Problem

It is very important in treatment of ophthalmic diseases including dry eye syndrome to develop a new preparation allowing a protein drug to penetrate into the eyes better than existing immunosuppressants, with fewer adverse effects. The present disclosure is directed to allowing easier cell transduction of FK506 binding protein (FK506BP), which binds to FK506 and effectively suppresses overactive immune response, as an effective means for protein therapy for ophthalmic diseases.

Technical Solution

The inventors of the present disclosure have developed a preparation of an immunosuppressive protein drug having enhanced ability to penetrate the eyes. As a result, they have developed an eye drop preparation for protein drugs effective for treating ophthalmic diseases.

The inventors have fused PEP-1 peptide or HIV-1 Tat peptide, which transduces native proteins into cells, at the N- and/or C-terminal of human FK506 binding protein (hereinafter, also referred to as FK506BP), over-expressed the fusion protein in *E. coli*, and purified the protein easily and conveniently through metal-chelating affinity chromatography. They have demonstrated through experiments that the purified fusion protein effectively improves ophthalmic diseases including xerophthalmia. Thus, the present disclosure provides the FK506BP fusion protein for use in protein therapy for ophthalmic diseases.

In one general aspect, the present disclosure provides an eye drop composition for prevention and treatment of ophthalmic diseases, including a fusion protein of FK506 binding protein wherein at least one of the N-terminal and C-terminal of FK506BP is covalently bonded to a protein transducing domain such as PEP-1 and Tat.

In another general aspect, the present disclosure provides a pharmaceutical composition for treating ophthalmic disease including xerophthalmia, including a fusion protein of FK506 binding protein. The fusion protein of FK506 binding protein according to the present disclosure is effective for treatment of ophthalmic diseases, particularly xerophthalmia.

As used herein, the term "ophthalmic disease" includes Stevens-Johnson syndrome, Sjogren syndrome, dry eye syndrome (xerophthalmia), ocular trauma, ocular trauma caused by eye surgery (Eye surgery refers to any surgery involving incision of the eye, typical examples including cataract surgery, glaucoma surgery, retinal surgery, laser-assisted in situ keratomileusis (LASIK), and laser-assisted sub-epithelial keratectomy), infectious/non-infectious uveitis, immune rejection after corneal transplantation, and exogenous corneal and conjunctival epithelial disorder caused by hard contact lenses. Although not intended to be limitative, such ophthalmic disease may include xerophthalmia.

As used herein, the term "xerophthalmia" refers to a medical condition in which the eye fails to produce enough tears or the tear film becomes unstable due to excessive evaporation, causing foreign body sensation or irritation. More specifically, "xerophthalmia" refers to a condition in which secretion of tears is reduced or which is accompanied by diseases of the eyeball and accessory organs, e.g. eyelid, such as disorder or inflammation of the eyelid, skin diseases (e.g., Stevens-Johnson syndrome or pemphigoid), or systemic diseases (e.g., vitamin A deficiency or Sjogren syndrome). The surface of the eye exposed between the eyelids may be damaged, resulting in discomfort, foreign body sensation, dryness, or the like. If the cornea is severely damaged, inflammation may occur on the ocular surface. Prolonged lesions may lead to congestion. Initial complications may include slight visual disorders, and corneal ulcer, corneal perforation and secondary infection in later stages. Corneal scarring and angiogenesis may lead to severe visual disorders.

The fusion protein of FK506 binding protein may be quantitatively or qualitatively analyzed according to genetic recombination, immunoassay based on antigen-antibody reactions (e.g., radioimmunoassay, radioimmunoprecipitation assay, enzyme-linked immunosorbent assay (ELISA), dot blot, Western blot, inhibition or competitive assay, and sandwich assay; See *Enzyme Immunoassay*, E. T. Maggio, ed., CRC Press, Boca Raton, Fla., 1980; and Gaastra, W., Enzyme-linked immunosorbent assay (ELISA), in *Methods in Molecular Biology*, Vol. 1, Walker, J. M. ed., Humana Press, NJ, 1984), molecular assay based on PCR, or the like.

The effect of the fusion protein of FK506 binding protein for ophthalmic disease according to the present disclosure may be demonstrated using published papers and a known xerophthalmia animal model.

For example, the inventors of the present disclosure used a dry air-induced rat dry eye model as a short-term xerophthalmia model. After surgically damaging an area of 0.4 mm$^2$ on the center portion of the cornea using a surgical knife, xerophthalmia was induced by exposing dry air of 25-30% humidity blown at 2.4 msec. Then, secretion of tears was measured according to Schirmer's test method. Also, corneal damage was evaluated using a fluorescent dye. Furthermore, the conjunctiva and palpebral conjunctiva were observed histopathologically, and apoptosis of corneal epithelial cells was evaluated immunohistochemically using poly(ADP-ribose) polymerase (PARP). In addition, the fusion protein of FK506 binding protein was compared with a 0.1% sodium hyaluronate eye drop, whose effect in treatment of xerophthalmia is proven (Johnson et al. 2006, 2008).

As another xerophthalmia model, a botulinum toxin-A (BTX-A)-induced mouse dry eye model was used. Xerophthalmia was induced by injecting 20 mU of BTX-A into the lachrymal gland through a transconjunctival route so that BTX-A was injected into the tear-secreting portion of the orbital lobe. Then, corneal damage was evaluated using a fluorescent dye, and the conjunctiva and palpebral conjunctiva were observed histopathologically.

For rat single-dose intravenous toxicity testing of the fusion protein of FK506 binding protein as a novel xerophthalmia-treating agent, an effective dose was determined as 0.01 mg/kg, which corresponds to 6 eye drops of a 0.1% solution. Toxicity testing was performed for a high-dosage group of 5 mg/kg, corresponding to 500 times the effective dose, and a low-dosage group of 2.5 mg/kg.

As a result, the FK506BP fusion protein according to the present disclosure remarkably increased secretion of tears in the dry eye animal model, increased the thickness of the conjunctival epithelium, which had been decreased due to inflammation, and resulted in increase of mucus producing cells. In addition, the FK506BP fusion protein according to the present disclosure reduced ocular damage-related apoptosis and corneal damage.

Hereinafter, the embodiments of the present disclosure will be described in detail with reference to accompanying drawings.

The present disclosure provides an eye drop composition for prevention and treatment of ophthalmic diseases comprising a fusion protein wherein at least one of the N-terminal and C-terminal of FK506 binding protein (FK506BP) is covalently bonded to a protein transducing domain.

The protein transducing domain may be one or more selected from:

a) a protein transducing domain comprising 15-30 amino acid residues and comprising a hydrophobic domain containing at least 5 tryptophans, a hydrophilic domain containing at least 4 lysines, and a spacer separating the two domains;

b) a protein transducing domain comprising 6-12 amino acid residues with ¾ or more of them being arginine or lysine residues;

c) an oligolysine protein transducing domain comprising 6-12 lysines;

d) an oligoarginine protein transducing domain comprising 6-12 arginines;

e) an oligo(lysine,arginine) protein transducing domain comprising 6-12 lysines or arginines; and derivatives thereof.

The fusion protein may be one or more selected from SEQ ID NO: 4, SEQ ID NO: 6, SEQ ID NO: 8, SEQ ID NO: 10, SEQ ID NO: 12 and SEQ ID NO: 14.

The ophthalmic disease may be Stevens-Johnson syndrome, Sjogren syndrome, dry eye syndrome (xerophthalmia), ocular trauma, ocular trauma caused by eye surgery, (infectious or non-infectious) uveitis, immune rejection after corneal transplantation, or exogenous corneal and conjunctival epithelial disorder caused by hard contact lenses.

The pharmaceutical composition comprising the FK506BP fusion protein as an active ingredient may be formulated into an eye drop preparation together with a pharmaceutically acceptable carrier according to a commonly employed method. The eye drop composition may be an isotonic aqueous solution or suspension, and may be sterilized and/or contain aids (e.g., preservatives, stabilizers, wetting agents, salt for adjusting osmotic pressure, and/or buffer) . In addition, it may contain other therapeutically useful substances.

Usually, an anionic polymer such as hyaluronate or carboxymethyl cellulose or a pharmaceutically acceptable salt thereof is used in the eye drop composition to provide moisturizing and lubricating effects. In addition, a pharmaceutically acceptable carrier may be included. The pharmaceutically acceptable carrier may include an isotonic agent, a buffer, a stabilizer, a pH adjusting agent, a solvent, or the like. The isotonic agent controls the isotonicity of the eye drop, and typical examples include sodium chloride, potassium chloride, and the like. The buffer controls the acidity or alkalinity of the eye drop. Typical examples of the buffer used in preparation of the eye drop include aminocaproic acid, dibasic sodium phosphate, monobasic sodium phosphate, and so forth. The stabilizer stabilizes the eye drop, and typically disodium ethylenediaminetetraacetate and/or sodium perborate may be used. The pH adjusting agent adjusts the pH of the eye drop composition. For example, hydrochloric acid and/or sodium hydroxide may be used. The solvent may be sterile purified water or sterile distilled water for injection. Specifically, the eye drop preparation according to the present disclosure may be a liquid formulation. The eye drop composition may further comprise an antiseptic, a preservative, or the like, if necessary.

The eye drop composition according to the present disclosure may be dropped on the eye 5-6 times a day, 1-3 drops each time. The dose may be adequately increased or decreased as needed. The dose for a particular patient would vary depending on the patient's body weight, age, sex and health, the period and number of administration, the severity of the disease, etc.

Intracellular transduction of the FK506BP protein molecule may be carried out by constructing a fusion protein wherein the N-terminal and/or C-terminal of FK506BP is covalently bonded to a protein transducing domain, the protein transducing domain comprising 15-30 amino acid residues and comprising a hydrophobic domain containing at least 5 tryptophans, a hydrophilic domain containing at least 4 lysines, and a spacer separating the two domains. An example of the transducing domain include the PEP-1 peptide (SEQ ID NO: 1) comprising 21 amino acids. And another protein transducing domain is the HIV Tat peptide residues 49-57 (SEQ ID NO: 2). However, the protein transducing domain of the present disclosure is not limited to the PEP-1 peptide of SEQ ID NO: 1 or the HIV Tat peptide residues 49-57 of SEQ ID NO: 2. Since those skilled in the art may easily prepare peptides performing similar functions to PEP-1 peptide or the HIV Tat peptide by replacing, adding or eliminating a portion of the sequence of PEP-1 or HIV Tat, it will be obvious that, in addition to the protein transducing domain comprising 15-30 amino acid residues and comprising a hydrophobic domain containing at least 5 tryptophans, a hydrophilic domain containing at least 4 lysines, and a spacer separating the two domains, a protein transducing domain comprising 6-12 amino acid residues with ¾ or more of them being arginine or lysine residues, an oligolysine protein transducing domain comprising 6-12 lysines, an oligoarginine protein transducing domain comprising 6-12 arginines, or an oligo(lysine,arginine) protein transducing domain comprising 6-12 lysines or arginines, which are prepared therefrom by replacing, adding or eliminating a portion of the sequence of PEP-1 or HIV Tat, are within the scope of the present disclosure.

Specifically, the present disclosure provides an eye drop composition for prevention and treatment of ophthalmic diseases comprising the FK506BP fusion protein covalently bonded to the protein transducing domain.

Definitions of major terms used in the present disclosure are as follows.

The "FK506BP fusion protein" refers to a covalently bonded complex comprising at least a protein transducing domain and a FK506BP. The protein transducing domain and a cargo molecule (i.e., FK506BP in the present disclosure) are fused genetically or chemically. In the specification and drawings, "fusion protein of FK506 binding protein" is synonymous with "FK506BP fusion protein". As a specific example, "PEP-1-FK506BP" refers to an FK506BP fusion protein wherein the PEP-1 protein transducing domain is bonded to the N-terminal of FK506BP.

"Genetic fusion" or "genetically fused" means a linear covalent linkage formed from the expression of a DNA sequence encoding a particular protein.

The "target cell" refers to a cell into which the cargo molecule is transduced by the transducing domain. That is to say, the target cell may be a cell constituting an organ or tissue of a living animal or human or a microorganism found in a living animal or human. The target cell also includes an external cell, i.e. cultured animal cell, human cell or microorganism. Specifically, the target cell means an ocular cell in this disclosure.

The "protein transducing domain" refers to a domain which forms a covalent bond with a peptide or protein, and allows the peptide or protein to be transduced into a cell without requiring additional receptors, carriers or energy. PEP-1 peptide (SEQ ID NO: 1) is an example.

The "target protein" refers to a molecule which forms a covalent bond with the PEP-1 protein transducing domain and exhibits activity when delivered into a cell. It is synonymous with "cargo molecule".

As used herein, "introduction" of a protein or peptide into a cell is synonymous with "transformation", "delivery", "penetration", "transduction", "transport" and "passing".

In the present disclosure, the protein transducing domain may be a protein transducing domain comprising 15-30 amino acid residues and comprising a hydrophobic domain containing at least 5 tryptophans, a hydrophilic domain containing at least 4 lysines, and a spacer separating the two domains, a protein transducing domain comprising 6-12 amino acid residues with ¾ or more thereof being arginine or lysine residues, an oligolysine protein transducing domain comprising 6-12 lysines, an oligoarginine protein transducing domain comprising 6-12 arginines, or an oligo(lysine, arginine) protein transducing domain comprising 6-12 lysines or arginines. Here, the target protein (cargo molecule) is FK506BP. At least one amino acid of the protein transducing domain and the target protein can be exchanged with a functionally equivalent amino acid of similar polarity in the sequence with silent change. Change in the amino acid sequence can be selected based upon the class to which the amino acid belongs. For example, hydrophobic amino acids include alanine, valine, leucine, isoleucine, phenylalanine, tryptophan, proline and methionine. Polar neutral amino acids include glycine, serine, threonine, cysteine, tyrosine, asparagine and glutamine. Positively-charged basic amino acids include arginine, lysine and histidine. Negatively-charged acidic amino acids include aspartic acid and glutamic acid. Segments or their derivatives having identical or similar biological activity with, for example, 85-100% amino acid sequence similarity to the fusion protein of the present disclosure are within the scope of the present disclosure.

The cell-transducing FK506BP fusion protein of the present disclosure may have an amino acid sequence of SEQ ID NO: 4, SEQ ID NO: 6, SEQ ID NO: 8, SEQ ID NO: 10, SEQ ID NO: 12 or SEQ ID NO: 14.

The protein transducing domain (PTD) of the present disclosure may be covalently bonded to at least one of the C-terminal and N-terminal of the FK506BP protein.

The present disclosure further provides an eye drop composition for treating ophthalmic diseases comprising the cell-transducing FK506BP fusion protein as an active ingredient.

The present disclosure further provides a composition comprising the cell-transducing FK506BP fusion protein as an active ingredient together with a pharmaceutically acceptable carrier.

Advantageous Effects

The FK506BP fusion protein according to the present disclosure significantly increases secretion of tears in a dry eye animal model.

Furthermore, the FK506BP fusion protein according to the present disclosure increases the thickness of the conjunctival epithelium, which has been decreased due to inflammation, and results in increase of mucus producing cells.

In addition, the FK506BP fusion protein according to the present disclosure reduces ocular damage-related apoptosis and corneal damage. With no special toxicity in in vivo toxicity test, it can be utilized for protein therapy for ophthalmic diseases.

DESCRIPTION OF DRAWINGS

The above and other objects, features and advantages of the present disclosure will become apparent from the following description of certain exemplary embodiments given in conjunction with the accompanying drawings, in which.

MODE FOR INVENTION

Figure 1:
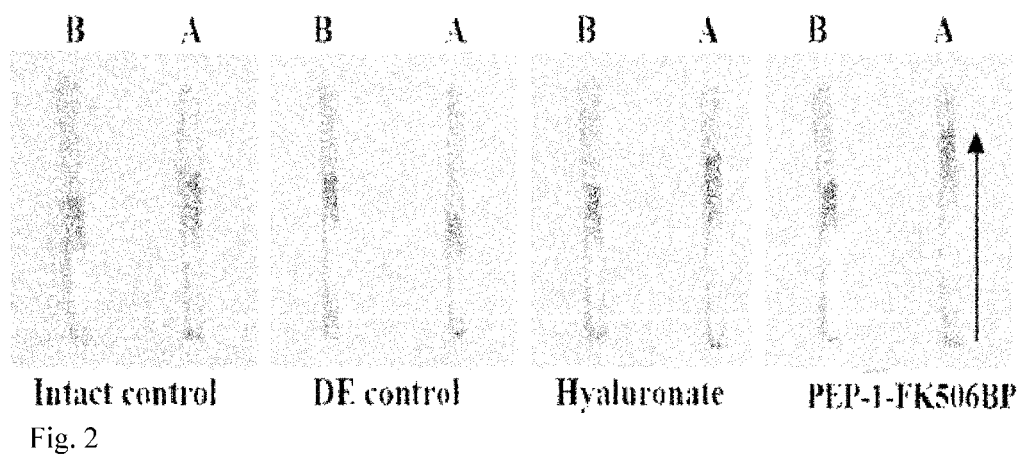
FIG. 1 shows a result of measuring secretion of tears before and after dry air blowing using 1×15 mm cobalt chloride paper according to Schirmer's test method (B: before dry air blowing, A: after dry air blowing. The normal control group (Intact) was not blown with dry air, and eye dryness was induced in the negative control group (DE control) by blowing with dry air but no drug was administered. The drug control group (Hyaluronate) was treated with hyaluronate, and the test group was treated with the FK506BP fusion protein of the present disclosure. Each drug was applied to the eye at a dose of 5 μL every hour for 5 hours.)

The examples and experiments will now be described. The following examples and experiments are for illustrative purposes only and it will be obvious to those skilled in the art that they do not to limit the scope of the present disclosure. In particular, although only the data about the PEP-1-FK506BP fusion protein among the various fusion proteins is described below, the other fusion proteins also exhibited similar (74-96%) results to the PEP-1-FK506BP fusion protein.

<Materials>

Restriction enzymes and T4 DNA ligase were purchased from Promega (USA), and Pfu polymerase was purchased from Stratagene (USA). Tat oligonucleotides were synthesized using a custom primer (Gibco BRL, USA). IPTG was purchased from Duchefa (the Netherlands). pET-15b and BL21(DE3) plasmids were purchased from Novagen (USA), and Ni-nitrilotriacetic acid sepharose superflow was purchased from Qiagen (Germany). The cDNA of human FK506 binding protein (FK506BP) was isolated from the human hepatic cDNA library by polymerase chain reaction (PCR). All other reagents were extra-pure grade.

Example 1

Construction and Transduction of PEP-1-FK506BP Fusion Protein Expression Vector

An expression vector for a fusion protein capable of transducing the functional target protein into the cell was constructed. Human FK506BP was selected as a target protein.

First, a pET-PEP expression vector containing PEP-1 peptide (KETWWE TWWTEW SQP KKKRKV, SEQ ID NO: 1) was constructed to produce the PEP-1-FK506BP fusion protein. Two kinds of oligonucleotides, corresponding to the PEP-1 peptide (top strand, 5'-TATGAAAGAAACCTG-GTGGGAAACCTGGTGGACCGAATGGTCTCAGC CGAAAAAAAAACGTAAAGTGC-3', SEQ ID NO: 15; bottom strand, 5'-TCGAGCACTTTACGTTTTTTTTTCG-GCTGACACCATTCGGTCCACCAGG TTTCCCACCAG-GTTTCTTTCC-3', SEQ ID NO: 16) were ligated into NdeI-Xho I-digested pET-15b vector. Next, two oligonucleotides were synthesized based on the cDNA sequence of human FK506BP. The forward primer 5'-CTCGAGATGGGAGTGC AGGTGGAAACCATC-3' (SEQ ID NO: 17) contained a Xho I restriction site, and the reverse primer 5'-GGATCCTCAT-TCCAGTTTTAGAAGCTCCAC-3' (SEQ ID NO: 18) contained a Bam HI restriction site.

PCR was performed in a thermocycler (Perkin-Elmer, model 9600). The reaction mixture was heated in a siliconized 50-μL reaction tube at 94° C. for 5 minutes. After PCR, the product was isolated by agarose gel electrophoresis and ligated into the TA cloning vector (Invitrogen, San Diego, USA), and a competent cell was transformed. Then, the plasmid was isolated from the transformed bacteria using the alkaline lysis method [Sambrook, J., Fritsch, F. E. and Maniatis, T. (1989) Molecular Cloning, Cold Spring Harbor Laboratory Press, Cold Spring Harbor]. The cDNA of human FK506BP was excised from the TA vector using Xho I and Bam HI, and inserted into the PEP expression vector. *E. coli* BL21 (DE3) transformed with the PEP-1-FK506BP was inoculated to 100 mL of LB medium and IPTG (0.5 mM) was added to the medium to induce overexpression of the recombined PEP-1-FK506BP fusion protein. The overexpressed PEP-1-FK506BP fusion protein was identified by SDS-polyacrylamide gel electrophoresis (SDS-PAGE) and Western blot analysis.

The FK506BP-PEP-1 fusion protein and the PEP-1-FK506BP-PEP-1 fusion protein were also prepared in a similar manner.

Example 2

Expression and Purification of PEP-1-FK506BP Fusion Protein

E. coli BL21 (DE3) cells transformed with the cDNA of human FK506BP using the PEP-1-FK506BP prepared in Example 1 were inoculated to LB medium containing ampicillin and cultured at 37° C. while stirring at 200 rpm. When the bacterial concentration ($OD_{600}$) in the culture medium reached 0.5-1.0, IPTG was added to the medium to a final concentration of 0.5 and 1 mM, and then the cells were further cultured for 12 hours at 30° C. The cells were harvested by centrifugation and then ultrasonicated in 5 mL of binding buffer (5 mM imidazole, 0.5 M NaCl, 20 mM Tris-HCl, pH 7.9). After centrifugation, the supernatant was immediately loaded onto a $Ni^{2+}$-nitrilotriacetic acid sepharose superflow column. After washing with 10 times the volume of binding buffer and 6 times the volume of washing buffer (60 mM imidazole, 0.5 M NaCl, 20 mM Tris-HCl, pH 7.9), the fusion protein was eluted with an elution buffer (1 M imidazole, 0.5 M NaCl, 20 mM Tris-HCl, pH 7.9). Subsequently, fractions containing the fusion protein were combined and salts were removed by PD-10 column chromatography.

The concentration of the purified protein was estimated by the Bradford method using bovine serum albumin as a standard [Bradford, M. A. (1976) *Anal. Biochem.* 72, 248-254].

The FK506BP-PEP-1 fusion protein and the PEP-1-FK506BP-PEP-1 fusion protein were overexpressed and purified in a similar manner.

Example 3

Construction and Transduction of Tat-FK506BP Fusion Protein Expression Vector

To overexpress a Tat-FK506BP fusion protein, the pET-Tat-FK506BP expression vector containing consecutive cDNA sequences encoding FK506BP, the HIV-1 Tat transduction domain (Tat 49-57) and six histidines was constructed. First, the pET-Tat expression vector having the basic domain of HIV-1 Tat (amino acids 49-57) was constructed. Two kinds of oligonucleotides, corresponding to the basic domain of Tat (top strand, 5'-TAGGAAGAAGCGGAGA-CAGCGACGAAGAC-3', SEQ ID NO: 19; bottom strand, 5'-TCGAGTCTTCGTCGCTGTCTCCGCTTCTTCC-3', SEQ ID NO: 20) were ligated into NdeI-Xho I-digested pET-15b vector. Next, two oligonucleotides were synthesized based on the cDNA sequence of human FK506BP. The forward primer (SEQ ID NO: 17) contained the Xho I restriction site, and the reverse primer (SEQ ID NO: 18) contained the Bam HI restriction site.

PCR was performed in a thermocycler (Perkin-Elmer, model 9600). The reaction mixture was heated in a siliconized 50-μL reaction tube at 94° C. for 5 minutes. The PCR consisted of 30 cycles of extension at 94° C. for 40 seconds, denaturation at 54° C. for 1 minute, and annealing at 70° C. for 3 minutes, followed by final extension at 72° C. for 10 minutes and at 20° C. for 5 minutes. After PCR, the product was isolated by agarose gel electrophoresis and ligated into the TA cloning vector (Invitrogen, San Diego, USA), and a competent cell was transformed. Then, the plasmid was isolated from the transformed bacteria using alkaline lysis. The cDNA of human FK506BP was excised from the TA vector using Xho I and Bam HI, and inserted into the pET-15b and pET-15b-Tat expression vectors. Expression is controlled by the T7 promoter and the lacO operator.

E. coli BL21 (DE3) transformed with the pET-Tat-FK506BP was inoculated to 100 mL of LB medium and IPTG (0.5 mM) was added to the medium to induce overexpression. Then, the E. coli cells were ultrasonicated at 4° C. and centrifuged. Then, the protein in the supernatant was isolated by 15% SDS-PAGE. The overexpressed FK506BP and Tat-FK506BP were identified by SDS-PAGE and Western blot analysis.

The FK506BP-Tat fusion protein and the Tat-FK506BP-Tat fusion protein were also prepared in a similar manner.

Example 4

Overexpression and Purification of Tat-FK506BP Fusion Protein

The transformed E. coli BL21 (DE3) cells were inoculated to LB medium containing ampicillin and cultured at 37° C. while stirring at 200 rpm. When the bacterial concentration ($OD_{600}$) in the culture medium reached 0.5-1.0, IPTG was added to the medium to reach a final concentration of 0.5 mM, and then the cells were further cultured for 3 hours. The cells were harvested by centrifugation and then ultrasonicated in 5 mL of binding buffer (5 mM imidazole, 0.5 M NaCl, 20 mM Tris-HCl, pH 7.9).

After centrifugation, the supernatant was immediately loaded onto a 2.5-mL $Ni^{2+}$-nitrilotriacetic acid sepharose superflow column. After washing with 10 times the volume of binding buffer and 6 times the volume of washing buffer (60 mM imidazole, 0.5 M NaCl, 20 mM Tris-HCl, pH 7.9), the fusion protein was eluted with elution buffer (1 M imidazole, 0.5 M NaCl, 20 mM Tris-HCl, pH 7.9). Subsequently, fractions containing the fusion protein were combined and salts were removed by Sephadex G-15 column chromatography. Since the fusion protein contains six consecutive histidines at the N-terminal, they could be purified almost purely (purity>90%) using one-step immobilized metal-chelate affinity chromatography. The concentration of the purified protein was estimated by the Bradford method using bovine serum albumin as the standard.

The FK506BP-Tat fusion protein and the Tat-FK506BP-Tat fusion protein were overexpressed and purified in a similar manner.

Example 5

Preparation of Sample

The purified FK506BP fusion proteins of Examples 2 and 4 were dissolved in physiological saline (5 μg/5 μL) and used as samples for tests.

Test Example 1

Change in Secretion of Tears in Dry Air-Induced Dry Eye Model Measured According to Schirmer's Test 1-1. Dry Air-Induced Dry Eye Animal Model After surgically damaging an area of 0.4 $mm^2$ on the center portion of the cornea of a rat using a surgical knife, the eye was exposed to dry air of humidity 25-30% blown at 2.4 m/sec to induce xerophthalmia.

1-2. Change in Secretion of Tears

Change in secretion of tears was measured according to Schirmer's test method using cobalt chloride paper (Toyo Roshi Kaisha, Japan). Schirmer's test method using phenol red thread is the most generally known method of measuring the change in secretion of tears. It is employed as the most basic experimental method of evaluating corneal dryness (Fujihara et al. 2001, *Invest. Ophthalmol. Vis. Sci.* 2001; 42: 96-100, Nakamura et al., *Cornea* 2004; 23: 390-7). In this example 1×15 mm cobalt chloride paper was used to determine change in secretion of tears before and after blowing dry air.

The xerophthalmia-induced control group exhibited significantly reduced secretion of tears as compared to the normal control group. When compared to the control drug hyaluronate (Samil Pharm. Co., Seoul, Korea), the test group treated with the FK506BP fusion protein of the present disclosure showed improved secretion of tears. Results are summarized in FIG. 1 and Table 1.

TABLE 1

| | | Secretion of tears (mm) | | |
|---|---|---|---|---|
| Groups | | Before test | After test | Change |
| Normal | Normal | 8.86 ± 0.97 | 10.19 ± 0.70 | 1.33 ± 1.15 |
| control group | Dry eye | 9.02 ± 1.50 | 7.65 ± 0.72 | −1.36 ± 1.43 |
| Drug control group | Hyaluronate | 8.95 ± 0.84 | 9.43 ± 1.52 | 0.48 ± 1.16 |
| Test group | FK506BP fusion protein | 8.98 ± 0.88 | 10.78 ± 1.02 | 1.80 ± 1.38 |

Test Example 2

Histopathological Change of Conjunctiva in Dry Air-Induced Dry Eye Model

After administration of the drug to the dry air-induced dry eye model, the conjunctiva was stained by periodic acid-Schiff (PAS) staining and observed histopathologically.

Figure 2:
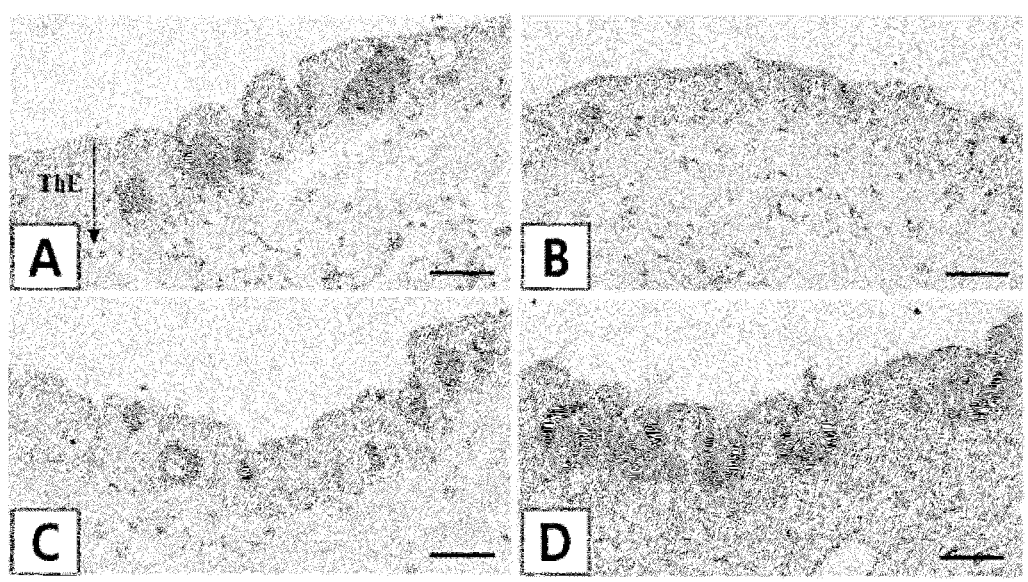
FIG. 2 show a result of histopathologically evaluating the effect of the FK506BP fusion protein on the thickness of the conjunctival epithelium and the number of mucus producing cells in a dry air-induced dry eye model through PAS staining (A: normal control group, B: negative control group dry eye-induced by blowing with dry air, C: drug control group treated with hyaluronate, D: test group treated with the FK506BP fusion protein. Each drug was applied to the eye at a dose of 5 μL every hour for 5 hours. In A, ThE denotes the thickness of the conjunctival epithelium.)

Xerophthalmia causes damage to the cornea and the conjunctiva, which can be easily observed histopathologically (Nakamura et al., *Invest. Ophthalmol. Vis. Sci.* 2003; 44: 4682-8, Higuchi et al., *Curr. Eye Res.* 2007; 32: 83-8). When compared to the normal group, the xerophthalmia-induced control group showed damage including partial loss of the conjunctival epithelium. Decreased thickness of the conjunctival epithelium, decreased number and proportion of mucus producing cells, and significant increase in the damaged area of the conjunctival epithelium were also observed. Such conjunctival damage was significantly reduced in the test group treated with the FK506BP fusion protein as compared to the xerophthalmia-induced control group. Results are summarized in Table 2 and FIG. 2.

TABLE 2

| | | | Mucus producing cells | |
|---|---|---|---|---|
| Groups | | Thickness of conjunctival epithelium (μm) | Number of cells/mm epithelium | Proportion (%)/mm epithelium |
| Normal | Normal | 113.21 ± 12.06 | 17.25 ± 3.15 | 40.03 ± 9.56 |
| control group | Dry eye | 38.13 ± 10.26 | 4.00 ± 1.93 | 10.02 ± 5.35 |
| Drug control group | Hyaluronate | 63.22 ± 10.53 | 8.63 ± 2.26 | 22.19 ± 7.02 |
| Test group | FK506BP fusion protein | 103.53 ± 15.12 | 14.88 ± 2.36 | 35.01 ± 9.66 |

Test Example 3

Change in Corneal Apoptosis in Dry Air-Induced Dry Eye Model

After administration of the drug to the dry air-induced dry eye model, apoptosis of the corneal epithelial cells was evaluated immunohistochemically using poly(ADP-ribose) polymerase (PARP).

PARP is a representative apoptotic marker (Barrett et al., *J. Histochem. Cytochem.* 2001; 49: 821-32). Increase of PARP in the corneal epithelium is indicative of increased damage to the corneal epithelium by apoptosis. It is known that the ocular damage caused by xerophthalmia is also related in part to apoptosis (Yeh et al., *Invest. Ophthalmol. Vis. Sci.* 2003; 44: 124-9).

Figure 3:
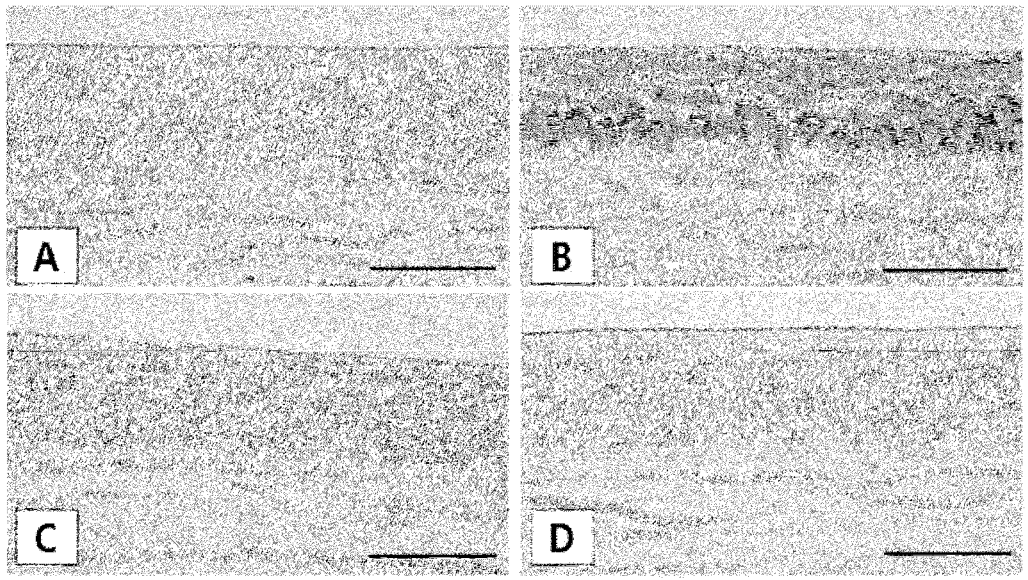
FIG. 3 shows results of immunohistochemically evaluating the degree of corneal apoptosis in a dry air-induced dry eye model using poly(ADP-ribose) polymerase (PARP) (A: normal control group, B: negative control group dry eye-induced by blowing with dry air, C: drug control group, D: test group treated with the FK506BP fusion protein of the present disclosure. Each drug was applied to the eye at a dose of 5 μL every hour for 5 hours. The scale bar in each figure is 80 μm long)

The xerophthalmia-induced control group showed significant increase of the apoptotic marker PARP as compared to the normal group. The test groups treated with the control drug hyaluronate or the FK506BP fusion protein showed similar decrease in apoptosis when compared with the xerophthalmia-induced control group. Results are summarized in FIG. 3.

Test Example 4

Degree of Corneal Damage in BTX-A-Induced Dry Eye Model 4-1. BTX-A-Induced Dry Eye Animal Model Xerophthalmia was induced in the botulinum toxin-A (BTX-A)-induced mouse dry eye model by injecting 20 mU of BTX-A into the lachrymal gland via the transconjunctival route so that BTX-A was injected into the tear-secreting portion of the orbital lobe.

4-2. Change in Permeability of Cornea to Fluorescent Dye

In order to investigate the effects of the FK506BP fusion protein on xerophthalmia, the degree of corneal damage of the BTX-A-induced xerophthalmia model was observed using a fluorescent dye (sodium salt of fluorescein, Sigma Co., USA).

Permeability of the cornea to a fluorescent dye is the most commonly employed method to evaluate cornea permeability. Increased permeability is known to be indicative of increased corneal damage (Yokoi & Kinoshita, *Cornea* 1995; 14: 485-9, Nakamura et al., *Invest. Ophthalmol. Vis. Sci.* 2003; 44: 4682-8, Nakamura et al., *Invest. Ophthalmol. Vis. Sci.* 2005; 46: 2379-87, Steinfeld et al., *Br. J. Ophthalmol.* 2004; 88: 48-53), and the damaged part of the cornea can be easily identified from the deposition or penetration of the fluorescent dye (Koh et al., *Am. J. Ophthalmol.* 2003; 136: 513-9).

Figure 4:
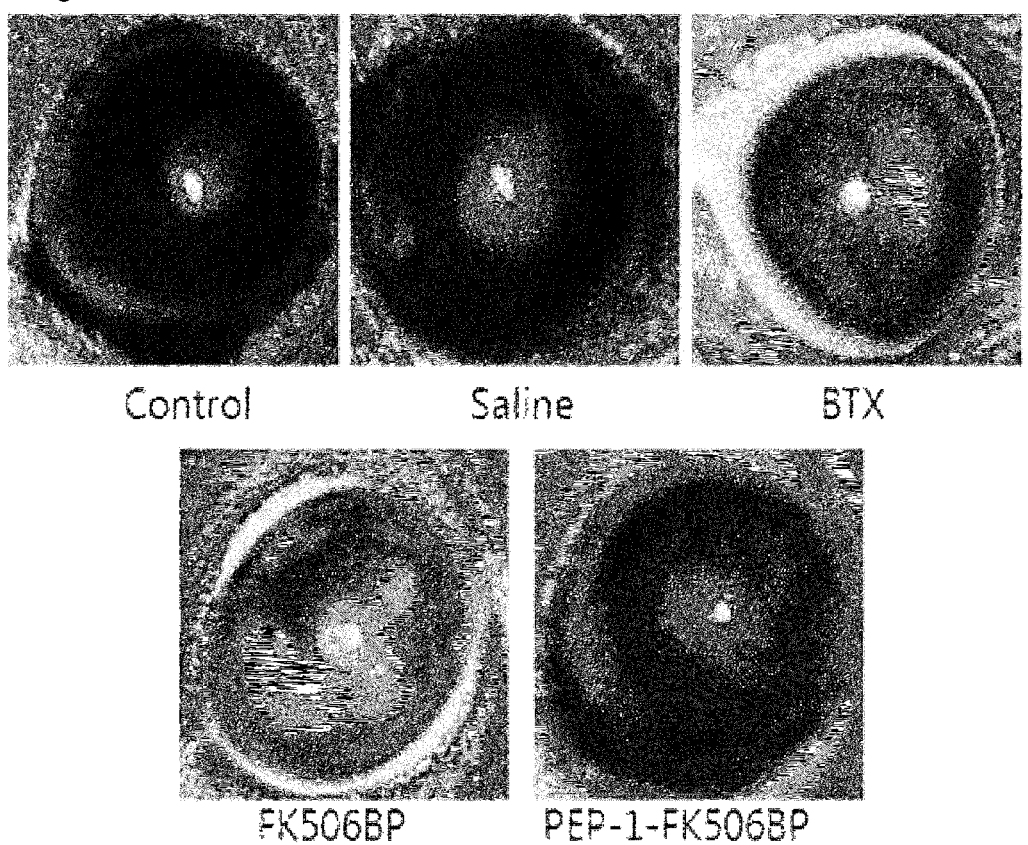
FIG. 4 shows slit lamp images of a BTX-A-induced xerophthalmia model taken using a fluorescent light source after dropping 1 μL of 1% fluorescein on the eye ("Control" is the normal control group, "Saline" is the control group treated with saline, "BTX" is the control group treated with BTX-A, "FK506BP" is the test group treated with FK506BP protein, not a fusion protein, and "PEP-1-FK506BP" is the test group treated with the fusion protein of FK506 binding protein. Each drug was applied to the eye at a dose of 5 μL every hour for 5 hours.).

The xerophthalmia-induced group showed greatly increased permeability of the cornea as compared to the normal group. Test groups were treated with the FK506BP protein or the FK506BP fusion protein. The FK506BP fusion protein group showed significantly decreased corneal permeability as compared to the FK506BP protein group. Results are summarized in FIG. 4.

Test Example 5

Rat Single-Dose Intravenous Toxicity Test of FK506BP Fusion Protein

For rat single-dose intravenous toxicity test of the FK506BP fusion protein as a novel xerophthalmia-treating agent, an effective dose was determined as 0.01 mg/kg, which corresponds to 6 eye drops of a 0.1% solution. Toxicity test was performed for a high-dosage group of 5 mg/kg, corresponding to 500 times of the effective dose, and a low-dosage group of 2.5 mg/kg. Each test group consisted of 5 rats.

Observations were made on mortality, clinical signs, body weight, postmortem findings, organ weight, histopathological change, etc. Seventeen organs were observed, including the lungs, heart, thymus, kidneys, adrenal gland, spleen, testicles/ovaries, liver, pancreas, brain, epididymis/uterus, submandibular lymph nodes, bladder, prostate gland, and tail vein where the administration had been made.

As a result, the FK506BP fusion protein resulted in death neither in the low-dosage group nor in the high-dosage group. It was confirmed to be very safe as an eye drop preparation, with no abnormality observed in terms of clinical signs, body weight, organ weight, and histopathological change.

Preparation Example 1

An eye drop composition comprising the FK506BP fusion protein was prepared as follows.

TABLE 3

| Ingredients | | Content (mg) |
| --- | --- | --- |
| Active ingredient | PEP-1-FK506BP | 5 |
| pH adjusting agent | Hydrochloric acid | adequate |
| | Sodium hydroxide | adequate |
| Isotonic agent | Sodium chloride | 700 |
| | Potassium chloride | 150 |
| Buffer | Aminocaproic acid | 200 |
| Stabilizer | Sodium edetate | 10 |
| Solvent | Sterile purified water | adequate |
| | Total | 100 mL |

Preparation Example 2

An eye drop composition comprising the FK506BP fusion protein was prepared as follows.

TABLE 4

| Ingredients | | Content (mg) |
| --- | --- | --- |
| Active ingredient | FK506BP-Tat | 5 |
| pH adjusting agent | Hydrochloric acid | adequate |
| | Sodium hydroxide | adequate |
| Isotonic agent | Sodium chloride | 700 |
| | Potassium chloride | 150 |
| Buffer | Aminocaproic acid | 200 |
| Stabilizer | Sodium edetate | 10 |
| Antiseptic | Benzalkonium chloride | 30 |
| Solvent | Sterile purified water | adequate |
| | Total | 100 mL |

INDUSTRIAL APPLICABILITY

The FK506BP fusion protein according to the present disclosure may be used for protein therapy for ophthalmic diseases.

SEQUENCE LIST PRETEXT

Primer sequences, protein-transducing domain sequences, and protein transducing domain-bound fusion protein sequences are shown in the attachment.

The invention claimed is:

1. A composition comprising a peptide selected from the group consisting of the amino acid sequence of SEQ ID NO: 4, SEQ ID NO: 6, SEQ ID NO: 8, SEQ ID NO: 10, SEQ ID NO: 12 and SEQ ID NO: 14.

2. The composition of claim 1, wherein the composition is formulated in an eye drop formula.

3. A method of treating Stevens-Johnson syndrome in a subject, the method comprising:
administering the composition of claim 1 to an eye of a subject that is in need of such treatment.

4. A method of treating Sjogren syndrome in a subject, the method comprising:
administering the composition of claim 1 to an eye of a subject that is in need of such treatment.

5. A method of treating dry eye syndrome (xerophthalmia) in a subject, the method comprising:
administering the composition of claim 1 to an eye of a subject that is in need of such treatment.

6. A method of treating ocular trauma in a subject, the method comprising:
administering the composition of claim 1 to an eye of a subject that is in need of such treatment.

7. A method of treating eye surgery induced ocular trauma in a subject, the method comprising:
administering the composition of claim 1 to an eye of a subject that is in need of such treatment.

8. A method of treating infectious or non-infectious uveitis in a subject, the method comprising:
administering the composition of claim 1 to an eye of a subject that is in need of such treatment.

9. A method of treating immune rejection after corneal transplantation in a subject, the method comprising:
administering the composition of claim 1 to an eye of a subject that is in need of such treatment.

10. A method of treating exogenous corneal and conjunctival epithelial disorder caused by hard contact lenses in a subject, the method comprising:
administering the composition of claim 1 to an eye of a subject that is in need of such treatment.

* * * * *

```
                        SEQUENCE LISTING

<160> NUMBER OF SEQ ID NOS: 20

<210> SEQ ID NO 1
<211> LENGTH: 21
<212> TYPE: PRT
<213> ORGANISM: Artificial Sequence
<220> FEATURE:
<223> OTHER INFORMATION: protein transducing domain called PEP-1

<400> SEQUENCE: 1

Lys Glu Thr Trp Trp Glu Thr Trp Trp Thr Glu Trp Ser Gln Pro Lys
  1               5                  10                  15

Lys Lys Arg Lys Val
            20

<210> SEQ ID NO 2
<211> LENGTH: 9
<212> TYPE: PRT
<213> ORGANISM: Human immunodeficiency virus type 1

<400> SEQUENCE: 2

Arg Lys Lys Arg Arg Gln Arg Arg Arg
  1               5

<210> SEQ ID NO 3
<211> LENGTH: 404
<212> TYPE: DNA
<213> ORGANISM: Artificial Sequence
<220> FEATURE:
<223> OTHER INFORMATION: nucleotide encoding PEP-1-FK506BP fusion
      protein
```

<400> SEQUENCE: 3

```
taaaagaaac ctggtgggaa acctggtgga ccgaatggtc tcagccgaaa aaaaaacgta     60
aagtgctcga gatgggagtg caggtggaaa ccatctcccc aggagacggg cgcaccttcc    120
ccaagcgcgg ccagacctgc gtggtgcact acaccgggat gcttgaagat ggaaagaaat    180
ttgattcctc ccgggacaga aacaagccct ttaagtttat gctaggcaag caggaggtga    240
tccgaggctg ggaagaaggg gttgcccaga tgagtgtggg tcagagagcc aaactgacta    300
tatctccaga ttatgcctat ggtgccactg gcacccagg catcatccca ccacatgcca    360
ctctcgtctt cgatgtggag cttctaaaac tggaatgagg atcc                     404
```

<210> SEQ ID NO 4
<211> LENGTH: 131
<212> TYPE: PRT
<213> ORGANISM: Artificial Sequence
<220> FEATURE:
<223> OTHER INFORMATION: PEP-1-FK506BP fusion protein

<400> SEQUENCE: 4

```
Lys Glu Thr Trp Trp Glu Thr Trp Trp Thr Glu Trp Ser Gln Pro Lys
 1               5                  10                  15
Lys Lys Arg Lys Val Leu Glu Met Gly Val Gln Val Glu Thr Ile Ser
            20                  25                  30
Pro Gly Asp Gly Arg Thr Phe Pro Lys Arg Gly Gln Thr Cys Val Val
        35                  40                  45
His Tyr Thr Gly Met Leu Glu Asp Gly Lys Lys Phe Asp Ser Ser Arg
    50                  55                  60
Asp Arg Asn Lys Pro Phe Lys Phe Met Leu Gly Lys Gln Glu Val Ile
65                  70                  75                  80
Arg Gly Trp Glu Glu Gly Val Ala Gln Met Ser Val Gly Gln Arg Ala
                85                  90                  95
Lys Leu Thr Ile Ser Pro Asp Tyr Ala Tyr Gly Ala Thr Gly His Pro
           100                 105                 110
Gly Ile Ile Pro Pro His Ala Thr Leu Val Phe Asp Val Glu Leu Leu
       115                 120                 125
Lys Leu Glu
       130
```

<210> SEQ ID NO 5
<211> LENGTH: 401
<212> TYPE: DNA
<213> ORGANISM: Artificial Sequence
<220> FEATURE:
<223> OTHER INFORMATION: nucleotide encoding FK506BP-PEP-1 fusion protein

<400> SEQUENCE: 5

```
atgggagtgc aggtggaaac catctcccca ggagacgggc gcaccttccc caagcgcggc     60
cagacctgcg tggtgcacta caccgggatg cttgaagatg gaaagaaatt tgattcctcc    120
cgggacagaa acaagccctt taagtttatg ctaggcaagc aggaggtgat ccgaggctgg    180
gaagaagggg ttgcccagat gagtgtgggt cagagagcca aactgactat atctccagat    240
tatgcctatg gtgccactgg gcacccaggc atcatcccac cacatgccac tctcgtcttc    300
gatgtggagc ttctaaaact ggaatgagga tcctaaaaga aacctggtgg gaaacctggt    360
ggaccgaatg gtctcagccg aaaaaaaaac gtaaagtgta g                         401
```

<210> SEQ ID NO 6
<211> LENGTH: 131
<212> TYPE: PRT
<213> ORGANISM: Artificial Sequence
<220> FEATURE:
<223> OTHER INFORMATION: FK506BP-PEP-1 fusion protein

<400> SEQUENCE: 6

```
Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu Lys Thr Trp
            100                 105                 110

Trp Glu Thr Trp Trp Thr Glu Trp Ser Gln Pro Lys Lys Lys Arg Lys
        115                 120                 125

Val Gly Ser
    130
```

<210> SEQ ID NO 7
<211> LENGTH: 472
<212> TYPE: DNA
<213> ORGANISM: Artificial Sequence
<220> FEATURE:
<223> OTHER INFORMATION: nucleotide encoding PEP-1-FK506BP-PEP-1 fusion protein

<400> SEQUENCE: 7

```
taaaagaaac ctggtgggaa acctggtgga ccgaatggtc tcagccgaaa aaaaaacgta      60
aagtgctcga gatgggagtg caggtggaaa ccatctcccc aggagacggg cgcaccttcc     120
ccaagcgcgg ccagacctgc gtggtgcact acaccgggat gcttgaagat ggaaagaaat     180
ttgattcctc ccgggacaga aacaagcccc ttaagtttat gctaggcaag caggaggtga     240
tccgaggctg ggaagaaggg gttgcccaga tgagtgtggg tcagagagcc aaactgacta     300
tatctccaga ttatgcctat ggtgccactg ggcacccagg catcatccca ccacatgcca     360
ctctcgtctt cgatgtggag cttctaaaac tggaatgagg atcctaaaag aaacctggtg     420
ggaaacctgg tggaccgaat ggtctcagcc gaaaaaaaaa cgtaaagtgt ag             472
```

<210> SEQ ID NO 8
<211> LENGTH: 154
<212> TYPE: PRT
<213> ORGANISM: Artificial Sequence
<220> FEATURE:
<223> OTHER INFORMATION: PEP-1-FK506BP-PEP-1 fusion protein

<400> SEQUENCE: 8

```
Lys Glu Thr Trp Trp Glu Thr Trp Trp Thr Glu Trp Ser Gln Pro Lys
1               5                   10                  15

Lys Lys Arg Lys Val Leu Glu Met Gly Val Gln Val Glu Thr Ile Ser
            20                  25                  30
```

Pro Gly Asp Gly Arg Thr Phe Pro Lys Arg Gly Gln Thr Cys Val Val
            35                  40                  45

His Tyr Thr Gly Met Leu Glu Asp Gly Lys Lys Phe Asp Ser Ser Arg
 50                  55                  60

Asp Arg Asn Lys Pro Phe Lys Phe Met Leu Gly Lys Gln Glu Val Ile
 65                  70                  75                  80

Arg Gly Trp Glu Glu Gly Val Ala Gln Met Ser Val Gly Gln Arg Ala
                 85                  90                  95

Lys Leu Thr Ile Ser Pro Asp Tyr Ala Tyr Gly Ala Thr Gly His Pro
            100                 105                 110

Gly Ile Ile Pro Pro His Ala Thr Leu Val Phe Asp Val Glu Leu Leu
            115                 120                 125

Lys Leu Glu Gly Ser Lys Glu Thr Trp Trp Glu Thr Trp Trp Thr Glu
    130                 135                 140

Trp Ser Gln Pro Lys Lys Lys Arg Lys Val
145                 150

<210> SEQ ID NO 9
<211> LENGTH: 366
<212> TYPE: DNA
<213> ORGANISM: Artificial Sequence
<220> FEATURE:
<223> OTHER INFORMATION: nucleotide encoding Tat-FK506BP fusion protein

<400> SEQUENCE: 9
aggaagaagc ggagacagcg acgaagactc gagatgggag tgcaggtgga aaccatctcc     60
ccaggagacg gccgcacctt ccccaagcgc ggccagacct gcgtggtgca ctacaccggg    120
atgcttgaag atggaaagaa atttgattcc tcccgggaca gaaacaagcc ctttaagttt    180
atgctaggca gcaggaggt gatccgaggc tgggaagaag ggttgcccca gatgagtgtg    240
ggtcagagag ccaaactgac tatatctcca gattatgcct atggtgccac tgggcaccca    300
ggcatcatcc caccacatgc cactctcgtc ttcgatgtgg agcttctaaa actggaatga    360
ggatcc                                                              366

<210> SEQ ID NO 10
<211> LENGTH: 119
<212> TYPE: PRT
<213> ORGANISM: Artificial Sequence
<220> FEATURE:
<223> OTHER INFORMATION: Tat-FK506BP fusion protein

<400> SEQUENCE: 10

Arg Lys Lys Arg Arg Gln Arg Arg Arg Leu Glu Met Gly Val Gln Val
  1               5                  10                  15

Glu Thr Ile Ser Pro Gly Asp Gly Arg Thr Phe Pro Lys Arg Gly Gln
             20                  25                  30

Thr Cys Val Val His Tyr Thr Gly Met Leu Glu Asp Gly Lys Lys Phe
         35                  40                  45

Asp Ser Ser Arg Asp Arg Asn Lys Pro Phe Lys Phe Met Leu Gly Lys
     50                  55                  60

Gln Glu Val Ile Arg Gly Trp Glu Glu Gly Val Ala Gln Met Ser Val
 65                  70                  75                  80

Gly Gln Arg Ala Lys Leu Thr Ile Ser Pro Asp Tyr Ala Tyr Gly Ala
                 85                  90                  95

Thr Gly His Pro Gly Ile Ile Pro Pro His Ala Thr Leu Val Phe Asp
            100                 105                 110

Val Glu Leu Leu Lys Leu Glu
        115

<210> SEQ ID NO 11
<211> LENGTH: 361
<212> TYPE: DNA
<213> ORGANISM: Artificial Sequence
<220> FEATURE:
<223> OTHER INFORMATION: nucleotide encoding FK506BP-Tat fusion protein

<400> SEQUENCE: 11

```
atgggagtgc aggtggaaac catctcccca ggagacgggc gcaccttccc caagcgcggc      60
cagacctgcg tggtgcacta caccgggatg cttgaagatg gaaagaaatt tgattcctcc     120
cgggacagaa acaagccctt taagtttatg ctaggcaagc aggaggtgat ccgaggctgg     180
gaagaagggg ttgcccagat gagtgtgggt cagagagcca aactgactat atctccagat     240
tatgcctatg gtgccactgg cacccaggc atcatcccac acatgccac tctcgtcttc       300
gatgtggagc ttctaaaact ggaaggatcc taggaagaag cggagacagc gacgaagata     360
g                                                                    361
```

<210> SEQ ID NO 12
<211> LENGTH: 117
<212> TYPE: PRT
<213> ORGANISM: Artificial Sequence
<220> FEATURE:
<223> OTHER INFORMATION: FK506BP-Tat fusion protein

<400> SEQUENCE: 12

Met Gly Val Gln Val Glu Thr Ile Ser Pro Gly Asp Gly Arg Thr Phe
  1               5                  10                  15

Pro Lys Arg Gly Gln Thr Cys Val Val His Tyr Thr Gly Met Leu Glu
             20                  25                  30

Asp Gly Lys Lys Phe Asp Ser Ser Arg Asp Arg Asn Lys Pro Phe Lys
         35                  40                  45

Phe Met Leu Gly Lys Gln Glu Val Ile Arg Gly Trp Glu Glu Gly Val
     50                  55                  60

Ala Gln Met Ser Val Gly Gln Arg Ala Lys Leu Thr Ile Ser Pro Asp
 65                  70                  75                  80

Tyr Ala Tyr Gly Ala Thr Gly His Pro Gly Ile Ile Pro Pro His Ala
                 85                  90                  95

Thr Leu Val Phe Asp Val Glu Leu Leu Lys Leu Glu Arg Lys Lys Arg
            100                 105                 110

Arg Gln Arg Arg Arg
        115

<210> SEQ ID NO 13
<211> LENGTH: 395
<212> TYPE: DNA
<213> ORGANISM: Artificial Sequence
<220> FEATURE:
<223> OTHER INFORMATION: nucleotide encoding Tat-FK506BP-Tat fusion
      protein

<400> SEQUENCE: 13

```
taggaagaag cggagacagc gacgaagact cgagatggga gtgcaggtgg aaaccatctc      60
cccaggagac gggcgcacct tccccaagcg cggccagacc tgcgtggtgc actacaccgg     120
gatgcttgaa gatggaaaga aatttgattc ctcccgggac agaaacaagc cctttaagtt     180
tatgctaggc aagcaggagg tgatccgagg ctgggaagaa ggggttgccc agatgagtgt     240
```

```
gggtcagaga gccaaactga ctatatctcc agattatgcc tatggtgcca ctgggcaccc    300
aggcatcatc ccaccacatg ccactctcgt cttcgatgtg gagcttctaa aactggaagg    360
atcctaggaa gaagcggaga cagcgacgaa gatag                               395
```

<210> SEQ ID NO 14
<211> LENGTH: 128
<212> TYPE: PRT
<213> ORGANISM: Artificial Sequence
<220> FEATURE:
<223> OTHER INFORMATION: Tat-FK506BP-Tat fusion protein

<400> SEQUENCE: 14

Arg Lys Lys Arg Arg Gln Arg Arg Arg Leu Glu Met Gly Val Gln Val
1               5                   10                  15

Glu Thr Ile Ser Pro Gly Asp Gly Arg Thr Phe Pro Lys Arg Gly Gln
            20                  25                  30

Thr Cys Val Val His Tyr Thr Gly Met Leu Glu Asp Gly Lys Lys Phe
        35                  40                  45

Asp Ser Ser Arg Asp Arg Asn Lys Pro Phe Lys Phe Met Leu Gly Lys
    50                  55                  60

Gln Glu Val Ile Arg Gly Trp Glu Glu Gly Val Ala Gln Met Ser Val
65                  70                  75                  80

Gly Gln Arg Ala Lys Leu Thr Ile Ser Pro Asp Tyr Ala Tyr Gly Ala
                85                  90                  95

Thr Gly His Pro Gly Ile Ile Pro Pro His Ala Thr Leu Val Phe Asp
            100                 105                 110

Val Glu Leu Leu Lys Leu Glu Arg Lys Lys Arg Arg Gln Arg Arg Arg
        115                 120                 125

<210> SEQ ID NO 15
<211> LENGTH: 68
<212> TYPE: DNA
<213> ORGANISM: Artificial Sequence
<220> FEATURE:
<223> OTHER INFORMATION: coding sequence for PEP-1

<400> SEQUENCE: 15

```
tatgaaagaa acctggtggg aaacctggtg gaccgaatgg tctcagccga aaaaaaaacg    60
taaagtgc                                                             68
```

<210> SEQ ID NO 16
<211> LENGTH: 70
<212> TYPE: DNA
<213> ORGANISM: Artificial Sequence
<220> FEATURE:
<223> OTHER INFORMATION: anticoding sequence for PEP-1

<400> SEQUENCE: 16

```
tcgagcactt tacgtttttt tttcggctga caccattcgg tccaccaggt ttcccaccag    60
gtttctttcc                                                           70
```

<210> SEQ ID NO 17
<211> LENGTH: 30
<212> TYPE: DNA
<213> ORGANISM: Artificial Sequence
<220> FEATURE:
<223> OTHER INFORMATION: primer

<400> SEQUENCE: 17

-continued

```
ctcgagatgg gagtgcaggt ggaaaccatc                                    30

<210> SEQ ID NO 18
<211> LENGTH: 30
<212> TYPE: DNA
<213> ORGANISM: Artificial Sequence
<220> FEATURE:
<223> OTHER INFORMATION: primer

<400> SEQUENCE: 18
ggatcctcat tccagtttta gaagctccac                                    30

<210> SEQ ID NO 19
<211> LENGTH: 29
<212> TYPE: DNA
<213> ORGANISM: Artificial Sequence
<220> FEATURE:
<223> OTHER INFORMATION: top strand for Tat peptide

<400> SEQUENCE: 19
taggaagaag cggagacagc gacgaagac                                     29

<210> SEQ ID NO 20
<211> LENGTH: 31
<212> TYPE: DNA
<213> ORGANISM: Artificial Sequence
<220> FEATURE:
<223> OTHER INFORMATION: bottom strand for Tat peptide

<400> SEQUENCE: 20
tcgagtcttc gtcgctgtct ccgcttcttc c                                  31
```